United States Patent [19]

Brennan

[11] 4,299,956
[45] Nov. 10, 1981

[54] METHOD OF MAKING N-(2-METHOXYETHYL)MORPHOLINE

[75] Inventor: Michael E. Brennan, Austin, Tex.

[73] Assignee: Texaco Inc., White Plains, N.Y.

[21] Appl. No.: 188,164

[22] Filed: Sep. 17, 1980

[51] Int. Cl.³ .......................................... C07D 295/08
[52] U.S. Cl. ................................................. 544/177
[58] Field of Search ........................ 544/177; 568/698

[56] References Cited

U.S. PATENT DOCUMENTS

| | | |
|---|---|---|
| 1,949,344 | 2/1934 | Woodhouse ........................ 568/698 |
| 2,014,408 | 9/1935 | Woodhouse ........................ 568/698 |
| 2,056,830 | 10/1936 | Coleman et al. ............... 568/698 X |
| 2,282,469 | 5/1942 | Frolich ................................ 568/698 |
| 3,267,156 | 8/1966 | Hansen ............................... 568/698 |

Primary Examiner—Joseph Paul Brust
Attorney, Agent, or Firm—Carl G. Ries; Robert A. Kulason; James L. Bailey

[57] ABSTRACT

Covers a process of making N-(2-methoxyethyl)morpholine by reacting N-(2-hydroxyethyl)morpholine with an excess of methanol in presence of a phosphorus-containing catalyst.

3 Claims, No Drawings

METHOD OF MAKING N-(2-METHOXYETHYL)MORPHOLINE

BACKGROUND OF THE INVENTION

1. Field of the Invention

The instant invention generally relates to an improved process for making N-(2-methoxyethyl)morpholine.

2. Prior Art

N-(2-methoxyethyl)morpholine has been found to be a very valuable chemical in the catalyst field. It has been found particularly useful as a polyurethane catalyst. However, known methods of preparing said chemical are relatively expensive usually involving a metal hydrogenation-dehydrogenation catalyst. One such method involves reaction of morpholine with ethylene glycol monomethyl ether in presence of hydrogen over said metal hydrogenation-dehydrogenation catalyst.

It would be a distinct advance in the art if finding a method of making N-(2-methoxyethyl)morpholine were found without need to resort to expensive metal hydrogenation-dehydrogenation catalyst and concomitant use of hydrogen. Such is the primary object of the present invention. Other objects will appear hereinafter.

SUMMARY OF THE INVENTION

In accordance with the broad aspects of the present invention N-(2-methoxyethyl)morpholine is produced by reacting N-(2-hydroxyethyl)morpholine with an excess of methanol in presence of a phosphorus-containing catalyst.

DESCRIPTION OF THE PREFERRED EMBODIMENTS

In accordance with the preferred embodiments N-(2-methoxyethyl)morpholine is prepared by reacting N-(2-hydroxyethyl)morpholine with an excess of methanol in presence of a phosphorus-containing catalyst. The reactants are readily available materials and need no further elaboration. Usually the reaction is effected at a relatively high temperature under pressure.

Suitable phosphorus-containing substances which can be employed include, for example, acidic metal phosphates, phosphoric acid compounds and their anhydrides, phosphorous acid compounds and anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

More particularly, suitable acidic metal phosphates include boron phosphate, ferric phosphate, aluminum phosphate, and the like.

Typical phosphoric acid compounds include aqueous or anydrous phosphoric acids such as orthophosphoric acid, pyrophosphoric acid, metaphosphoric acid, hypophosphoric acid, and condensed phosphoric acids such as polyphosphoric acids. Accordingly, an example of a suitable phosphorous acid is orthophosphorous acid. Additionally, phosphoric acid-impregnated silicas having from about 10 to about 30 wt.% phosphoric acid may be employed.

In addition, any commercially available mono-, di-, or tri-alkyl or aryl phosphate or phosphite ester can be employed as the catalyst in the inventive process. Additionally, bis(phosphates) and secondary phosphate esters such as those disclosed in U.S. Pat. Nos. 3,869,526 and 3,869,527, respectively, can be used. Preferably, the lower alkyl esters are employed such as those having from 1 to about 8 carbon atoms per alkyl group. Preferred aryl esters contain from about 6 to about 20 carbon atoms and may include a phenyl group or alkyl-substituted phenyl group.

Further, suitable alkyl or aryl substituted phosphorous and phosphoric acids which may be employed as a catalyst include alkyl phosphonic acids, aryl phosphonic acids, alkyl phosphinic acids and aryl phosphinic acids. Preferably, such acids include alkyl groups having from 1 to about 8 carbon atoms and/or aryl groups having from about 6 to about 20 carbon atoms in each alkyl or aryl group respectively.

Specific examples of alkyl and aryl substituted phosphorous and phosphoric acids that may be used in accordance with the invention are phenylphosphinic acid, ethylphosphonic acid, phenylphosphonic acid, naphthaphosphonic acid, and methylphosphinic acid. Examples of arlkyl and aryl substituted phosphorous and phosphoric acid esters are methylphenyl phosphonate, dimethylphenyl phosphonate, methylphenyl phosphinate, ethyl naphthaphosphinate, and propylmethyl phosphonate. When phosphorous acid is employed, it is preferably used in anhydrous form or in an aqueous solution having from about 10 to about 70 wt.% phosphorous acid. The aqueous phosphorous acid catalyst is miscible with the reactants and is, therefore, a homogeneous catalyst.

The above mentioned phosphorus-containing substances are not intended to be exhaustive of those that can be employed as a catalyst in the instant inventive process. Those materials set forth are merely intended to be representative of the types of substances that have been found to be particularly effective. Of the substances and the types of compounds mentioned, it is particularly preferred to employ those that are known to be most reactive, such as orthophosphoric acids, polyphosphoric acids, boron phosphate, aluminum phosphate, ferric phosphate, and orthophosphorous acid. Of these, the most preferred are orthophosphorous acid and aluminum phosphate.

The phosphoric acid-impregnated silicas, ferric phosphate, boron phosphate, and aluminum phosphate and other phosphorous-containing catalysts are effective catalysts when employed in an amount of from about 1 to about 20% based upon the amount of reactants. An aqueous phosphorous acid catalyst is slightly more active than the other catalysts and is generally employed in an amount of from about 1 to about 10 wt.%, based on the reactants present, with an amount of from about 2.5 to about 5.0 wt.%, on the same basis, being preferred.

The reaction of this invention, as described herein, is carried out substantially in a liquid phase reaction which is conducted at a temperature of from about 200° C. to about 350° C., more often 250°–350° C. It has been found that temperatures in the range of from about 260° C. to 300° C. are normally sufficient for good yield production of the desire morpholine derivative.

The pressure at which the reaction is carried out can be at any pressure sufficient to maintain the reactants substantially in the liquid state. Generally, reaction pressures of from about 10 to about 3,000 psig. have been found satisfactory.

It has been found that for the typical reaction temperatures the preferable reaction zone pressure is from about 1000 to about 2000 psig.

In practicing the process of this invention a solvent is not required, but may be employed if desired. Whenever a solvent is employed, the solvent should be non-deleterious to the reaction environment and the desired reaction. Examples of suitable solvents include hydrocarbon solvents such as hexane, decance, dodecene, benzene, and the like, and chlorinated aromatic solvents such as chlorobenzene.

The crude reaction product obtained from the process of this invention will contain the desired N-(2-methoxyethyl)morpholine (MEM) in combination with some 2,2'-dimorpholine diethyl ether (DMDEE) and 2,2'-dimorpholine ether (DMORE) and larger amounts of N-methylmorpholine (NMM). It has been found that the catalyst may be recovered from the crude reaction mixture and recycled for reuse according to the process of this invention. In the case of heterogeneous catalysts, excepting the phosphoric acid-impregnated silicas, it is generally preferable to wash the recovered catalyst, for example with methanol and/or water, and dry it prior to recycling it for reuse. In the case of the aqueous phosphorous acid catalyst, it may be recovered and reconstituted to the desired concentration prior to reuse as a salt and reused as such.

The N-(2-methoxyethyl)morpholine can be recovered from the crude reaction mixture by conventional means, for example distillation, extraction, and the like.

The reaction is usually run in an excess of methanol at a mole ratio of methanol to morpholine derivative of 1.5:1 to 10:1.

The process of this invention will now be further illustrated in the following examples which are set forth for the purpose of illustration and should not be considered as a limitation upon the scope of the invention.

EXAMPLES 1–6

A clean and dry 1 liter stirred stainless steel autoclave was charged with a solution of 262.3 g (2.0 moles) N-(2-hydroxyethyl)morpholine (HEM) and 256.0 g (8.0 moles) methanol and then the phosphorus-containing catalyst. After purging and padding with nitrogen, the autoclave was sealed and then heated to the desired temperature and held for the below indicated length of time. After cooling to room temperature, the autoclave was carefully vented and the reaction mixture recovered. Results are based on Glc anaylysis and Karl Fisher water determination. Products were identified by distillation and spectral characterization and results were given below in Table 1.

TABLE I

| Run No. | Temp. °C. | Press. psig | t hrs. | % HEM Conv. | % Selectivity | | | |
|---|---|---|---|---|---|---|---|---|
| | | | | | NMM | MEM | DMDEE | DMORE |
| A. 5.0 wt. % AlPO$_4$ | | | | | | | | |
| 1 | 300 | 1475–1720 | 3.0 | 95.1 | 60.0 | 25.1 | 0.7 | 0.2 |
| 2 | 290 | 1350–1375 | 3.0 | 88.6 | 52.2 | 28.2 | 1.1 | 0.2 |
| 3 | 280 | 1200–1265 | 3.0 | 83.0 | 50.9 | 30.1 | 1.7 | 0.2 |
| B. 0.53 mole % 30% aq. phosphorous acid (H$_3$PO$_3$) | | | | | | | | |
| 4 | 300 | 1510–1710 | 2.0 | 95.6 | 61.0 | 22.5 | 0.5 | 0.2 |
| 5 | 290 | 1300–1390 | 2.0 | 88.1 | 50.3 | 22.6 | 0.8 | 0.2 |
| 6 | 280 | 1235–1260 | 2.0 | 84.5 | 55.3 | 27.9 | 1.3 | 0.5 |

The invention is hereby claimed as follows:

1. A process for making N-(2-methoxyethyl)morpholine which comprises condensing N-(2-hydroxyethyl)morpholine with an excess of methanol in presence of a phosphorus-containing catalyst selected from the group consisting of acidic metal phosphates, phosphoric acids and their anhydrides, or phosphorous acids and their anhydrides, alkyl or aryl phosphate esters, alkyl or arylphosphite esters, alkyl or aryl substituted phosphorous acids and phosphoric acids, alkali metal monosalts of phosphoric acid, thioanalogs of the foregoing, and mixtures thereof at a temperature of 250° to 350° C., and under a pressure ranging from about 1000 psig to about 2000 psig, the amount of said phosphorus-containing catalyst ranging from about 1 percent to about 10 percent based on the weight of reactants, and the mole ratio of methanol to N-(2-hydroxyethyl)morpholine ranging from 1.5:1 to 10:1.

2. The process of claim 1 wherein said phosphorus-containing catalyst is aluminum phosphate.

3. The process of claim 1 wherein said phosphorus-containing catalyst is phosphorous acid.

* * * * *